United States Patent
Chu

(10) Patent No.: US 9,144,483 B2
(45) Date of Patent: Sep. 29, 2015

(54) PLACING FIXATION DEVICES

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1420 days.

(21) Appl. No.: 11/331,777

(22) Filed: Jan. 13, 2006

(65) Prior Publication Data

US 2007/0173864 A1    Jul. 26, 2007

(51) Int. Cl.
*A61B 17/04* (2006.01)
*A61F 2/00* (2006.01)
*A61B 17/062* (2006.01)
*A61B 17/00* (2006.01)
*A61B 17/06* (2006.01)
*A61B 17/29* (2006.01)

(52) U.S. Cl.
CPC ............ *A61F 2/0045* (2013.01); *A61B 17/0401* (2013.01); *A61B 17/0469* (2013.01); *A61B 17/0482* (2013.01); *A61B 17/0625* (2013.01); *A61B 2017/00805* (2013.01); *A61B 2017/0409* (2013.01); *A61B 2017/0412* (2013.01); *A61B 2017/0417* (2013.01); *A61B 2017/0427* (2013.01); *A61B 2017/0437* (2013.01); *A61B 2017/0464* (2013.01); *A61B 2017/06052* (2013.01); *A61B 2017/06176* (2013.01); *A61B 2017/2927* (2013.01)

(58) Field of Classification Search
USPC .................. 128/885; 606/139, 140, 141, 151; 600/29, 30, 37; 623/23.72
See application file for complete search history.

(56) References Cited

U.S. PATENT DOCUMENTS

| | | |
|---|---|---|
| 669,034 A | 2/1901 | Manly |
| 2,687,131 A | 8/1954 | Raiche |
| 3,123,077 A | 3/1964 | Alcamo |
| 4,083,369 A | 4/1978 | Sinnreich |
| 4,324,331 A | 4/1982 | Ignasiak |
| 4,792,336 A | 12/1988 | Hlavacek et al. |
| 4,919,667 A | 4/1990 | Richmond |
| 4,979,956 A * | 12/1990 | Silvestrini .................. 623/13.11 |
| 4,998,912 A | 3/1991 | Scarbrough et al. |
| 5,013,292 A | 5/1991 | Lemay |
| 5,082,112 A | 1/1992 | Dunklee |
| 5,112,344 A | 5/1992 | Petros |
| 5,149,329 A | 9/1992 | Richardson |

(Continued)

FOREIGN PATENT DOCUMENTS

| | | |
|---|---|---|
| DE | 10056169 A1 | 6/2002 |
| EP | 0088714 A1 | 9/1983 |

(Continued)

OTHER PUBLICATIONS

"Capio® Suture Capturing Devices," *Reach, Throw and Capture: One Step. One Device*, Boston Scientific, www.bostonscientific.com, one page, 2005.

(Continued)

*Primary Examiner* — Dianne Dornbusch

(57) ABSTRACT

A fixation device can be delivered to the body of a patient by coupling the fixation device to a delivery instrument at a head of the fixation device. Engaging the fixation device to the delivery instrument at the fixation device's head allows the fixation device to be secured to a tissue and/or ligament of the patient. The fixation device can be a sling for placement around the bladder neck of a female patient.

11 Claims, 11 Drawing Sheets

(56) References Cited

U.S. PATENT DOCUMENTS

| | | |
|---|---|---|
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,364,408 A | 11/1994 | Gordon |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,464,409 A | 11/1995 | Mohajer |
| 5,474,518 A | 12/1995 | Velazquez |
| 5,485,917 A | 1/1996 | Early |
| 5,527,341 A | 6/1996 | Gogolewski et al. |
| 5,534,008 A | 7/1996 | Acksel |
| 5,540,704 A * | 7/1996 | Gordon et al. ............... 606/144 |
| 5,562,689 A | 10/1996 | Green et al. |
| 5,569,283 A | 10/1996 | Green et al. |
| 5,575,800 A | 11/1996 | Gordon |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon et al. |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,899,909 A | 5/1999 | Claren et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A * | 1/2000 | Kardjian ...................... 600/29 |
| 6,012,580 A | 1/2000 | Peters et al. |
| 6,039,686 A | 3/2000 | Kovac |
| 6,042,534 A * | 3/2000 | Gellman et al. ............... 600/30 |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,195,646 B1 | 2/2001 | Grosh et al. |
| 6,197,036 B1 | 3/2001 | Tripp et al. |
| 6,200,330 B1 | 3/2001 | Benderev et al. |
| 6,221,005 B1 * | 4/2001 | Bruckner et al. ............... 600/30 |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,897 B1 * | 6/2003 | Ory et al. ...................... 600/30 |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar |
| 6,595,911 B2 | 7/2003 | LoVuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 * | 9/2003 | Staskin et al. ................... 600/30 |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,872,227 B2 * | 3/2005 | Sump et al. ................... 623/13.2 |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 * | 8/2006 | Tannhauser ................... 606/228 |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |
| 7,402,133 B2 | 7/2008 | Chu et al. |

(56) References Cited

U.S. PATENT DOCUMENTS

| | | |
|---|---|---|
| 7,413,540 B2 | 8/2008 | Gellman et al. |
| 7,527,588 B2 | 5/2009 | Zaddem et al. |
| 7,878,970 B2 | 2/2011 | Goldberg |
| 8,128,552 B2 * | 3/2012 | O'Donnell ............... 600/30 |
| 2001/0023356 A1 | 9/2001 | Raz et al. |
| 2001/0049467 A1 | 12/2001 | Lehe et al. |
| 2002/0007222 A1 | 1/2002 | Desai |
| 2002/0010457 A1 | 1/2002 | Duchon et al. |
| 2002/0028980 A1 | 3/2002 | Thierfelder et al. |
| 2002/0099259 A1 | 7/2002 | Anderson et al. |
| 2002/0128670 A1 | 9/2002 | Ulmsten et al. |
| 2002/0143234 A1 | 10/2002 | LoVuolo |
| 2002/0147382 A1 | 10/2002 | Neisz et al. |
| 2002/0151909 A1 | 10/2002 | Gellman et al. |
| 2002/0156489 A1 | 10/2002 | Gellman et al. |
| 2003/0009181 A1 | 1/2003 | Gellman et al. |
| 2003/0023138 A1 | 1/2003 | Luscombe |
| 2003/0023250 A1 | 1/2003 | Watschke et al. |
| 2003/0055313 A1 | 3/2003 | Anderson et al. |
| 2003/0078604 A1 | 4/2003 | Walshe |
| 2003/0125715 A1 | 7/2003 | Kuehn et al. |
| 2003/0149334 A1 | 8/2003 | Ulmsten et al. |
| 2003/0176762 A1 | 9/2003 | Kammerer |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 * | 12/2003 | Benderev ............... 606/151 |
| 2003/0233108 A1 | 12/2003 | Gellman et al. |
| 2004/0006353 A1 | 1/2004 | Bosley et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1 | 2/2004 | Gellman et al. |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0073234 A1 | 4/2004 | Chu et al. |
| 2004/0087970 A1 * | 5/2004 | Chu et al. ............... 606/119 |
| 2004/0106847 A1 | 6/2004 | Benderev |
| 2004/0116944 A1 | 6/2004 | Chu et al. |
| 2004/0133217 A1 | 7/2004 | Watschke |
| 2004/0138747 A1 | 7/2004 | Kaladelfos |
| 2004/0181243 A1 | 9/2004 | Chu et al. |
| 2004/0186515 A1 | 9/2004 | Rosenblatt |
| 2004/0225181 A1 | 11/2004 | Chu et al. |
| 2004/0230206 A1 | 11/2004 | Gellman et al. |
| 2004/0231678 A1 * | 11/2004 | Fierro ............... 128/885 |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0004427 A1 | 1/2005 | Cervigni |
| 2005/0004576 A1 | 1/2005 | Benderev |
| 2005/0038451 A1 | 2/2005 | Rao et al. |
| 2005/0038452 A1 | 2/2005 | Chu |
| 2005/0075660 A1 | 4/2005 | Chu et al. |
| 2005/0080317 A1 | 4/2005 | Merade |
| 2005/0090706 A1 | 4/2005 | Gellman et al. |
| 2005/0096499 A1 | 5/2005 | Li et al. |
| 2005/0101834 A1 | 5/2005 | Merade |
| 2005/0107805 A1 | 5/2005 | Bouffier et al. |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0192600 A1 | 9/2005 | Nicolo et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0250978 A1 | 11/2005 | Kammerer |
| 2005/0256366 A1 | 11/2005 | Chu |
| 2005/0256530 A1 | 11/2005 | Petros |
| 2005/0261545 A1 | 11/2005 | Gellman et al. |
| 2005/0261547 A1 | 11/2005 | Bouffier |
| 2005/0277807 A1 | 12/2005 | MacLean et al. |
| 2005/0278037 A1 | 12/2005 | Delorme et al. |
| 2006/0015001 A1 | 1/2006 | Staskin et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0041263 A1 | 2/2006 | Chu et al. |
| 2006/0052801 A1 | 3/2006 | Dreyfuss et al. |
| 2006/0058574 A1 | 3/2006 | Priewe et al. |
| 2006/0058575 A1 | 3/2006 | Zaddem et al. |
| 2006/0069301 A1 | 3/2006 | Neisz et al. |
| 2006/0089524 A1 | 4/2006 | Chu |
| 2006/0089525 A1 * | 4/2006 | Mamo et al. ............... 600/37 |
| 2006/0122457 A1 | 6/2006 | Kovac et al. |
| 2006/0173237 A1 | 8/2006 | Jacquetin |
| 2006/0205995 A1 | 9/2006 | Browning |
| 2006/0211911 A1 | 9/2006 | Jao et al. |
| 2006/0229596 A1 | 10/2006 | Weiser et al. |
| 2006/0264698 A1 | 11/2006 | Kondonis et al. |
| 2007/0043255 A1 * | 2/2007 | O'Donnell ............... 600/30 |
| 2007/0055095 A1 | 3/2007 | Chu et al. |
| 2007/0161849 A1 | 7/2007 | Goldberg et al. |
| 2007/0173864 A1 | 7/2007 | Chu |
| 2007/0270890 A1 | 11/2007 | Miller et al. |
| 2007/0276358 A1 | 11/2007 | Barzell et al. |
| 2011/0098527 A1 | 4/2011 | Goldberg |
| 2014/0179987 A1 | 6/2014 | Miller |

FOREIGN PATENT DOCUMENTS

| | | |
|---|---|---|
| EP | 0141589 A1 | 5/1985 |
| EP | 0299158 A1 | 1/1989 |
| EP | 0362146 A1 | 4/1990 |
| EP | 0412664 A1 | 2/1991 |
| EP | 0774240 A1 | 5/1997 |
| EP | 1201189 A2 | 5/2002 |
| EP | 1508305 A2 | 2/2005 |
| EP | 1520554 A2 | 4/2005 |
| EP | 1609439 A1 | 12/2005 |
| EP | 1933786 A2 | 6/2008 |
| EP | 1978891 A1 | 10/2008 |
| EP | 2617385 A2 | 7/2013 |
| EP | 1998711 B1 | 12/2013 |
| FR | 2785521 A1 | 5/2000 |
| FR | 2852817 A1 | 10/2004 |
| FR | 2852818 A1 | 10/2004 |
| FR | 2871365 A1 | 12/2005 |
| JP | 06114067 A2 | 4/1994 |
| JP | 08501005 | 2/1996 |
| JP | 11514266 | 12/1997 |
| MX | PA04008407 A | 12/2005 |
| WO | 9405213 A1 | 3/1994 |
| WO | 9713465 A1 | 4/1997 |
| WO | 98/35616 A1 | 8/1998 |
| WO | 98/35632 A1 | 8/1998 |
| WO | 99/37216 A1 | 7/1999 |
| WO | 00/09039 A1 | 2/2000 |
| WO | 00/74594 A1 | 12/2000 |
| WO | 00/74613 A1 | 12/2000 |
| WO | 01/06951 A1 | 2/2001 |
| WO | 01/52135 A1 | 7/2001 |
| WO | 02/31681 A1 | 4/2002 |
| WO | 02/32284 A2 | 4/2002 |
| WO | 02/38079 A2 | 5/2002 |
| WO | 02/058563 A1 | 8/2002 |
| WO | 02/062237 A1 | 8/2002 |
| WO | 02/078571 A2 | 10/2002 |
| WO | 03002027 A1 | 1/2003 |
| WO | 03/068107 A1 | 8/2003 |
| WO | 03/073960 A1 | 9/2003 |
| WO | 03/096928 A1 | 11/2003 |
| WO | 03/096929 A1 | 11/2003 |
| WO | 2004/016196 A2 | 2/2004 |
| WO | 2004012626 A1 | 2/2004 |
| WO | 2004/091442 A2 | 10/2004 |
| WO | 2004/091443 A2 | 10/2004 |
| WO | 2005122954 A1 | 6/2005 |
| WO | WO 2005/051204 | 6/2005 |
| WO | 2005/122721 A2 | 12/2005 |

(56) References Cited

FOREIGN PATENT DOCUMENTS

| WO | 2005/122954 A1 | 12/2005 |
|---|---|---|
| WO | WO 2005/122954 | 12/2005 |
| WO | 2006/046950 A1 | 5/2006 |
| WO | 2007/014240 A1 | 2/2007 |
| WO | 2007/016698 A2 | 2/2007 |
| WO | 2007/019374 A2 | 2/2007 |
| WO | 2007/038589 A2 | 4/2007 |
| WO | 2007/059199 A2 | 5/2007 |
| WO | 2007/087132 A1 | 8/2007 |
| WO | 2007087132 A1 | 8/2007 |

OTHER PUBLICATIONS

"Capio® Open Access and Standard Suture Capturing Devices," *Reach, Throw and Capture: One Step. One Device*, Boston Scientific, www.bostonscientific.com, two pages, printed on Apr. 7, 2006.
"Capio® CL Transvaginal Suture Capturing Device," *Designed for Transvaginal Suture Fixation to Cooper's Ligament for Sling Procedures*, Boston Scientific, www.bostonscientific.com, one page, 2001.
"Capio® CL Transvaginal Suture Capturing Device," *The Capio CL Transvaginal Suture Capturing Device allows for a transvaginal suture fixation to Cooper's Ligament for Sling Procedures*, Boston Scientific, www.bostonscientific.com, two pages, printed on Apr. 7, 2006.
"Capio® RP Suture Device," *The Capio RP Suturing Device is designed to assist with anastomosis after a radical prostatectomy*, Boston Scientific, www.bostonscientific.co.uk, one page, undated.
"Capio® RP Suture Device," Boston Scientific, www.bostonscientific.co.uk, one page, printed on Apr. 7, 2006.
International Search Report and Written Opinion of the International Searching Authority in International Application No. PCT/US2007/000190, which claims priority to U.S. Appl. No. 11/331,777 (15 pages).
Notification Concerning Transmittal of International Preliminary Report on Patentability (Chapter 1 of the Patent Cooperation Treaty) mailed Jul. 24, 2008 issued in corresponding international application No. PCT/US2007/000190.
Amendment and Response to Final Office Action with RCE for U.S. Appl. No. 11/686,683, filed May 18, 2010, 14 pages.
Partial European Search Report for EP Application No. 10189230.5, mailed Dec. 10, 2010, 6 pages.
European Office Action for EP Application No. 07716311.1, mailed Dec. 8, 2009, 3 pages.
Search report for French Patent Application No. FR 0303895, mailed on Jan. 21, 2004, 3 pages.
Search report for French Patent Application No. FR 0303893, mailed on Jan. 21, 2004, 2 pages.
Search Report for European Patent Application No. EP 05356101, mailed on Nov. 1, 2005, 2 pages.
Search report for French Patent Application No. FR0406352, mailed on May 25, 2007, 3 pages.
Search Report for European Patent Application No. EP 90307704, mailed on Apr. 18, 2007, 1 page.
Search Report for EP Patent Application No. EP 01117717, mailed on Apr. 18, 2007, 5 pages.
International Search Report for PCT Application No. PCT/US2001/031234, mailed on Dec. 14, 2001, 1 page.
International Search Report for Application No. PCT/FR2004/000766, mailed on Nov. 8, 2004, 9 pages.
International Search Report for PCT Application No. PCT/US2006/028963, mailed on Dec. 6, 2006, 3 pages.
International Search Report for PCT Application No. PCT/US2007/000190, mailed on Jul. 3, 2007, 5 pages.
International Search report for PCT Application No. PCT/US2004/035329, mailed on Jul. 7, 2005, 7 pages.
International Search Report for PCT Application No. PCT/US2001/30033, mailed on May 10, 2002, 1 page.
International Search Report for PCT Application No. PCT/US1998/03066, mailed on May 28, 1998, 2 pages.
International Search Report for International Application No. PCT/FR2004/000765, mailed on Dec. 28, 2004, 10 pages.
Office Action received for U.S. Appl. No. 11/686,683, mailed on Jul. 8, 2009, 17 pages.
Office Action received for U.S. Appl. No. 11/535,901, mailed on Jan. 29, 2009, 22 pages.
Response to Office Action for U.S. Appl. No. 11/535,901, filed Oct. 9, 2009, 12 pages.
Office Action for U.S. Appl. No. 11/535,901, mailed on Jun. 9, 2009, 22 pages.
Response to Restriction Requirement for U.S. Appl. No. 11/535,901, filed May 14, 2009, 2 pages.
Restriction Requirement for U.S. Appl. No. 11/535,901, mailed on Apr. 14, 2009, 9 pages.
Response to Office Action for U.S. Appl. No. 11/493,148, filed Mar. 17, 2010, 13 pages.
Response to Office Action for U.S. Appl. No. 11/493,148, filed Sep. 1, 2009, 12 pages.
Response to Office Action for U.S. Appl. No. 11/493,148, filed Feb. 19, 2009, 12 pages.
Office Action for U.S. Appl. No. 11/493,148, mailed on Sep. 24, 2008, 14 pages.
Office Action for U.S. Appl. No. 11/493,148, mailed on Jun. 5, 2009, 14 pages.
Office Action for U.S. Appl. No. 11/493,148, mailed on Dec. 17, 2009, 13 pages.
Office Action for U.S. Appl. No. 11/493,148, mailed on Mar. 25, 2010, 14 pages.
Response to Office Action for U.S. Appl. No. 11/686,683, filed Oct. 6, 2009, 11 pages.
Office Action for U.S. Appl. No. 11/686,683, mailed on Jan. 19, 2010, 15 pages.
Notice of Allowance for U.S. Appl. No. 11/535,901, mailed Sep. 21, 2010, 26 pages.
Response to Office Action for U.S. Appl. No. 11/535,901, filed Oct. 9, 2009. 12 pages.
Office Action for U.S. Appl. No. 11/535,901, mailed on Jan. 29, 2009, 22 pages.
Office Action for U.S. Appl. No. 11/686,683, mailed on Jul. 8, 2009, 17 pages.
Response to Office Action for U.S. Appl. No. 11/686,683, filed May 18, 2010, 13 pages.
Non-Final Office Action for U.S. Appl. No. 12/983,666, mailed Oct. 6, 2011, 47 pages.
Office Action for EP Application No. 07758616.2, mailed on Jun. 6, 2011, 5 pages.
Final Office Action for U.S. Appl. No. 12/983,666, mailed Apr. 24, 2012, 10 pages.
Office Action Response for U.S. Appl. No. 12/983,666, filed Jul. 24, 2012, 2 pages.
Final Office Action Response for U.S. Appl. No. 12/983,666, filed Jun. 25, 2012, 8 pages.
Non-Final Office Action Response for U.S. Appl. No. 12/983,666, filed Feb. 3, 2012, 9 pages.
Non-Final Office Action for U.S. Appl. No. 12/983,666, mailed Jul. 30, 2013, 10 pages.
Non-Final Office Action Response for U.S. Appl. No. 12/983,666, filed Oct. 30, 2013, 8 pages.
Hardiman, et al, "Sacrospinous Vault Suspension and Abdominal Colposacropexy: Success Rates and Complications", Section of Urogynecology, Department of Obstetrics and Gynecology, University of Toronto, Mount Sinai Hospital, Sep. 18, 1995, 5 pages.
Pohl, et al, "Bilateral Transvaginal Sacrospinous Colpopexy: Preliminary Experience", 23rd Annual Meeting of the Society of Gynecologic Surgeons, Feb. 24-26, 1997, 7 pages.
Shah, et al, "Short-Term Outcome Analysis of Total Pelvic Reconstruction With Mesh: The Vaginal Approach", The Journal of Urology, vol. 171, Jan. 2004, pp. 261-263.
Final Office Action for U.S. Appl. No. 11/686,683, mailed Nov. 5, 2012, 32 pages.
Non-Final Office Action for U.S. Appl. No. 11/686,683, mailed Aug. 13, 2013, 26 pages.

(56) References Cited

OTHER PUBLICATIONS

Final Office Action Response for U.S. Appl. No. 11/686,683, filed Feb. 5, 2013, 17 pages.
Extended EP Search Report for EP Application No. 10189230.5, mailed Mar. 31, 2011, 11 pages.
Non-Final Office Action for U.S. Appl. No. 11/686,683, mailed Apr. 26, 2012, 17 pages.
Non-Final Office Action Response for U.S. Appl. No. 11/686,683, filed Aug. 27, 2012, 13 pages.
Final Office Action for U.S. Appl. No. 11/686,683, mailed Feb. 25, 2014, 29 pages.
Office Action for CA Application No. 2,636,215, mailed on Apr. 17, 2013, 3 pages.
Office Action Response for CA Application No. 2,636,215, filed on Oct. 16, 2013, 4 pages.
Office Action for EP Application No. 07758616.2, mailed Jun. 6, 2011, 5 pages.
Office Action Response for JP Application No. 2008-550341, filed Apr. 26, 2012, 10 pages.
Office Action for JP Application No. 2008-550341, mailed Jan. 27, 2012, 3 pages.
Office Action for JP Application No. 2008-550341, mailed Jul. 12, 2012, 2 pages.
Response to Final Office Action for U.S. Appl. No. 11/686,683, filed May 23, 2014, 12 pages.
Non-Final Office Action for U.S. Appl. No. 11/686,683, mailed on Jun. 17, 2014, 31 pages.
Final Office Action for U.S. Appl. No. 12/983,666, mailed on May 30, 2014, 13 pages.
Office Action for CA Application No. 2,636,215, mailed on Jan. 13, 2014, 2 pages.
Office Action for EP Application No. 10189230.5, mailed on Mar. 31, 2014, 5 pages.
Office Action for JP Application No. 2012226178 (with Translation), mailed on Jun. 11, 2014, 5 pages.
Response to Communication pursuant to Article 94(3) EPC for EP Patent Application 10189230.5, filed on Jul. 24, 2014, 7 pages.
Extended European Search Report for European Patent Application No. 13164488.2, mailed on Jul. 31, 2014, 6 pages.
Response to Communication pursuant to Article 94(3) EPC for EP Patent Application 06815573.8, filed on Aug. 13, 2014, 15 pages.
Response to Office Action for Japanese Patent Application No. 2012-226178, filed on Sep. 11, 2014, 14 pages.
Office Action for Canadian Patent Application No. 2,636,215, mailed on Nov. 13, 2014, 4 pages.
Notice of Allowance for U.S. Appl. No. 11/493,148, mailed on Sep. 30, 2010, 6 pages.
Response to Final Office Action for U.S. Appl. No. 11/686,683, filed Sep. 17, 2014, 13 pages.
Response to Non-Final Office Action for U.S. Appl. No. 12/983,666, filed Nov. 25, 2014, 9 pages.
Final Office Action for U.S. Appl. No. 11/686,683, mailed on Dec. 23, 2014, 18 pages.

* cited by examiner

PLACING FIXATION DEVICES

TECHNICAL FIELD

The invention generally is directed to the placement of a fixation device within the body of a patient.

BACKGROUND INFORMATION

Conditions such as rectocele, cystocele, enterocele, vaginal prolapse, and protocele involve tissues or organs that have been damaged, prolapsed, weakened, or otherwise herniated. A prolapse refers to the slipping of an organ, or organ part, from its normal position. For example, a prolapse of the rectum refers to the protrusion of the rectum through the anus. Rectocele is the prolapse of the rectum into the perineum. A prolapse of the uterus refers to the falling of the uterus into the vagina due to stretching and laxity of its supporting structures. Vaginal vault prolapse refers to the prolapse of the cephalad extreme of the vaginal wall toward, through, and beyond the introitus. Cystocele (i.e., vesicocele) is a hernia formed by the downward and backward displacement of the urinary bladder toward the vaginal orifice, due most commonly to weakening of the musculature during childbirth. However, any abnormal descent of the anterior vaginal wall and bladder base at rest or with strain is considered cystocele. Enterocele is a hernia of the intestine, though the term is also used to refer specifically to herniation of the pelvic peritoneum through the rectouterine pouch (i.e., posterior vaginal, rectovaginal, cul-de-sac, or Douglas' pouch hernia). Proctocele is a prolapse of the mucous coat of the rectum due mostly from relaxation of the sphincter. Treatment of these conditions frequently requires a sling, such as a mesh sling, implanted at the anatomical site-requiring repair.

Stress urinary incontinence (SUI) primarily affects women and generally is caused by two conditions that may occur independently or in combination, namely, intrinsic sphincter deficiency (ISD) and hypermobility. In ISD, the urinary sphincter valve, located within the urethra, fails to close properly, causing urine to leak out of the urethra during stressful actions. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.), resulting in insufficient response time to promote urethral closure and, consequently, in urine leakage and/or flow.

Biological factors that may affect hypermobility include: poor endopelvic fascia muscle tone (from, for example, age or limited activity), endopelvic fascia muscle stretch/tear from trauma (e.g., childbirth), endopelvic fascia/arcus tendenious (muscle/ligament) separation (lateral defect), hormone (e.g., estrogen) deficiency, concombinant defects (e.g., cystocele, enterocele, and ureteral prolapse), and vaginal prolapse. Traditional treatment methods include urethra or bladder neck stabilization slings in which a sling is placed under the mid-urethra or bladder neck to provide a platform preventing over distention.

Slings are traditionally placed under the urethra or bladder neck to provide a urethral platform limiting endopelvic fascia drop while providing compression to the urethral sphincter to improve coaptation. The urethral placement location provides mechanical stability to a less moveable anatomical structure. Bladder neck slings traditionally have been affixed in the desired location using a bone anchoring method. Mid-urethral slings, being placed in a low mobility area, may be placed using an anchorless approach. Recognizing that minimal tension, if any, is necessary, a physician may need only to secure a mid-urethra sling through the endopelvic fascia. The sling in this placement provides a fulcrum about which the pelvic floor will drop (taking advantage of the hypermobility condition of the patient) and a urethral "kink" or higher resistance to obstruct urine flow during high stress conditions.

A known method for stabilizing organs and tissues within the pelvic region involves the use of bone anchors. Deployment of a bone anchor requires drilling a hole in a bone, either by using a separate drilling instrument or by utilizing the anchor itself as a drilling tool. Bone anchors generally have one or more barbs that project outward to prevent the anchor from exiting the hole. Such anchors generally are not amenable to implantation in soft tissues, since the barbs would tear the soft tissue, causing irritation and/or passage of the anchor back through the tissue.

Other known methods include making one or more incisions in a patient's abdomen. For example, one method for treating female stress urinary incontinence involves supporting the urethra with an implant anchored in the patient's skin after the implant has been passed through the skin of the patient's abdomen.

SUMMARY OF THE INVENTION

Illustrative embodiments according to the invention are directed towards securing a fixation device to a treatment area within the body of a patient such as a human or other mammal. Some embodiments are directed towards a fixation device sized to be coupled to a delivery instrument for delivering the fixation device to a treatment area within the body by coupling the fixation device to the delivery instrument at a fixation device head of the instrument. Coupling the fixation device to the head of the delivery instrument allows the fixation device to be delivered to a tissue and/or ligament within the body and subsequently secured to that tissue and/or ligament.

In one aspect, the invention relates to an instrument for delivering a fixation device to a tissue comprises a distal portion including a carrier capable of extending from a retracted position to an extended position upon actuation by a user. The carrier comprises a side slot which allows the carrier to receive a fixation device. A shaft of the fixation device passes through the slot of the carrier, and a fixation device head is positioned at a distal end of the carrier. The instrument also comprises a catch for securing the fixation device head once the fixation device head has been driven through the tissue as the carrier moves from the retracted position to the extended position.

In another aspect, the invention involves a fixation device comprises a head engaged to a shaft. The head and the shaft are sized to be received by an extendable carrier of a delivery instrument, and the head is sized to be secured within a catch of the delivery instrument. A sling can be engaged to the shaft of the fixation device.

In yet another aspect, the invention features a sling which comprises a first fixation device engaged to a first end of the sling. The first fixation device can comprise a head of the first fixation device engaged to a shaft. The head and the shaft are sized to be received by an extendable carrier of a delivery instrument, and the head is sized to be secured within a catch of the delivery instrument. A plurality of the fixation devices can be engaged to the sling.

BRIEF DESCRIPTION OF THE DRAWINGS

The disclosed embodiments will be further explained with reference to the attached drawings, wherein like structures are referred to by like numerals throughout the several views. The drawings are not necessarily to scale, the emphasis having instead been generally placed upon illustrating the principles of the invention and the disclosed embodiments.

DESCRIPTION

Illustrative embodiments according to the invention are directed towards a fixation device and an instrument and method for securing the fixation device to a treatment area. More specifically, particular illustrative embodiments described herein are directed towards a fixation device sized to be coupled to a delivery instrument, and a method of delivering the fixation device to a treatment area by coupling the fixation device to the delivery instrument at a fixation device head. Coupling the fixation device to the delivery instrument at the fixation device head allows the fixation device to be delivered and secured to a tissue and/or ligament.

In one embodiment, a method for the placement of a sling material involves engaging a first fixation device to a first end of a sling material and engaging a second fixation device to a second end of the sling material. The fixation device head of the first fixation device is engaged to an extendable carrier of the delivery instrument. Next, the fixation device head of the first fixation device is pushed through a tissue and/or ligament and the fixation device head is secured in a catch of the delivery instrument. Once the head of the fixation device is secured in the catch, the delivery instrument is withdrawn from the tissue a desired distance in order to further secure the fixation device to the tissue at a desired tension. The head of the first fixation device head then is disengaged from the delivery instrument.

Once the first fixation device is secured in the tissue, the head of the second fixation device is engaged to the extendable carrier of the delivery instrument. As such, the second fixation device may be delivered to a second desired location in the same manner as described above. A plurality of fixation devices can be engaged to a sling material, and each fixation device is thereby delivered to the treatment area. Any number of fixation devices engaged to a sling material (or any other material) are within the scope of the present invention.

Figure 1A:
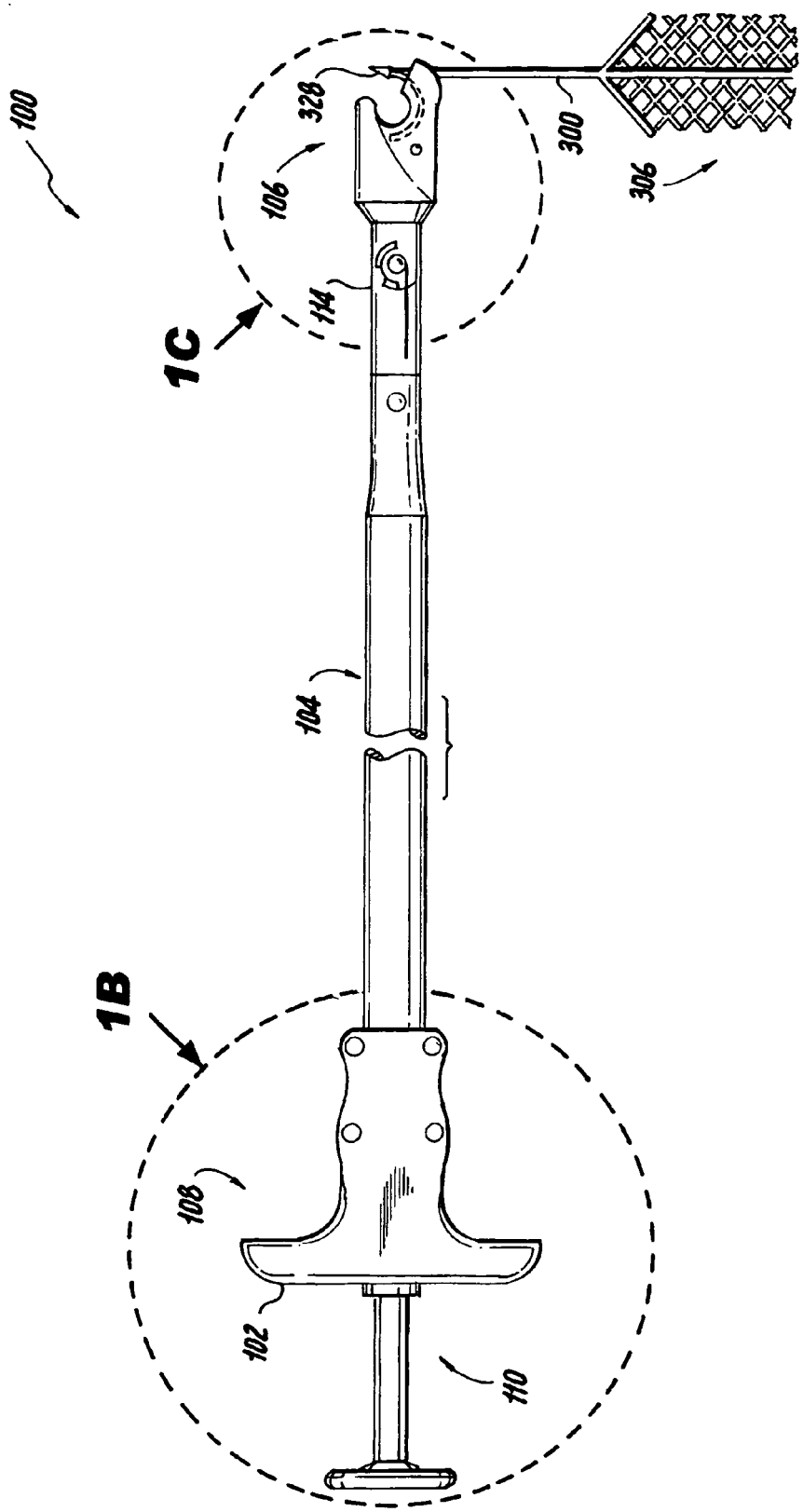
FIG. 1A is a schematic plan view of an embodiment of a delivery instrument engaged to an embodiment of a presently disclosed fixation device.
Figure 1B:
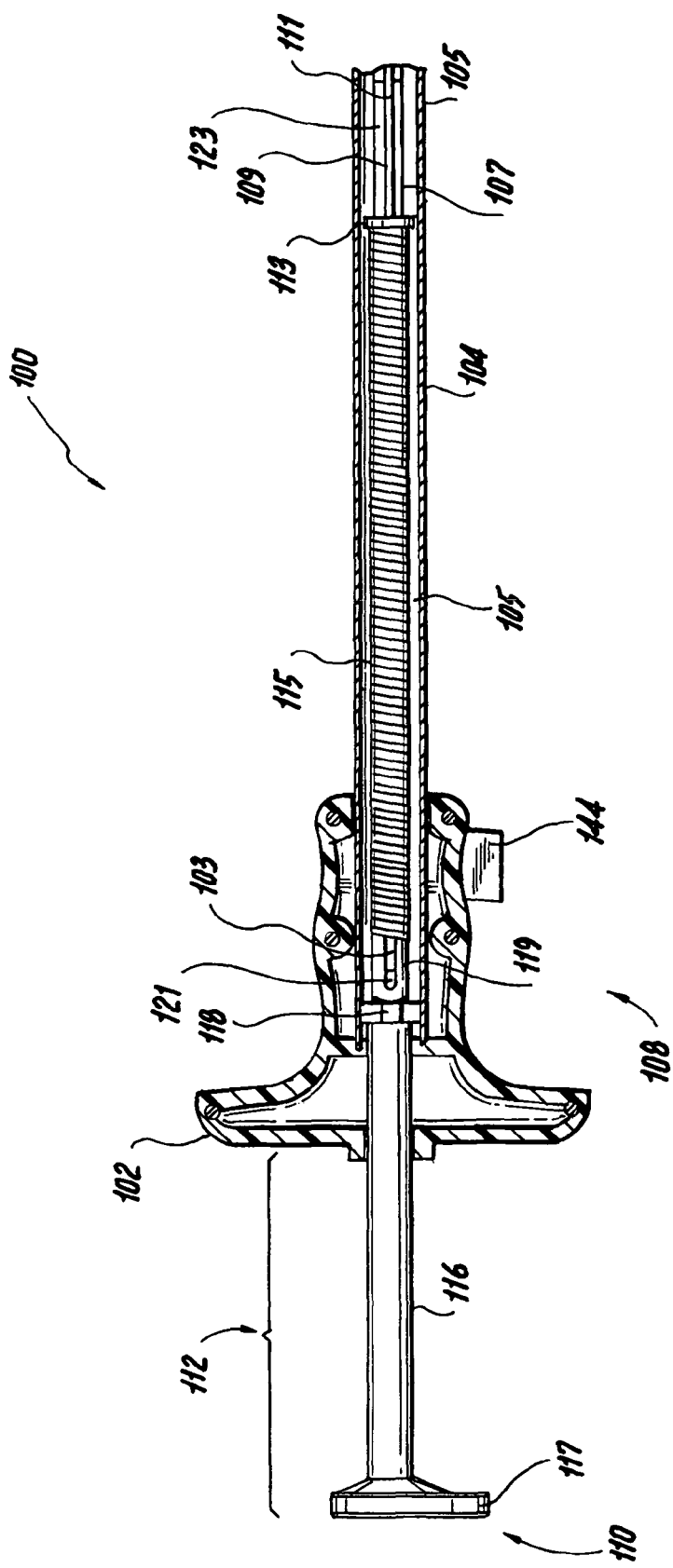
FIGS. 1B and 1C (fixation device not attached) are schematic cross-sectional views of a proximal portion and a distal portion of the delivery instrument of FIG. 1A.
Figure 1C:
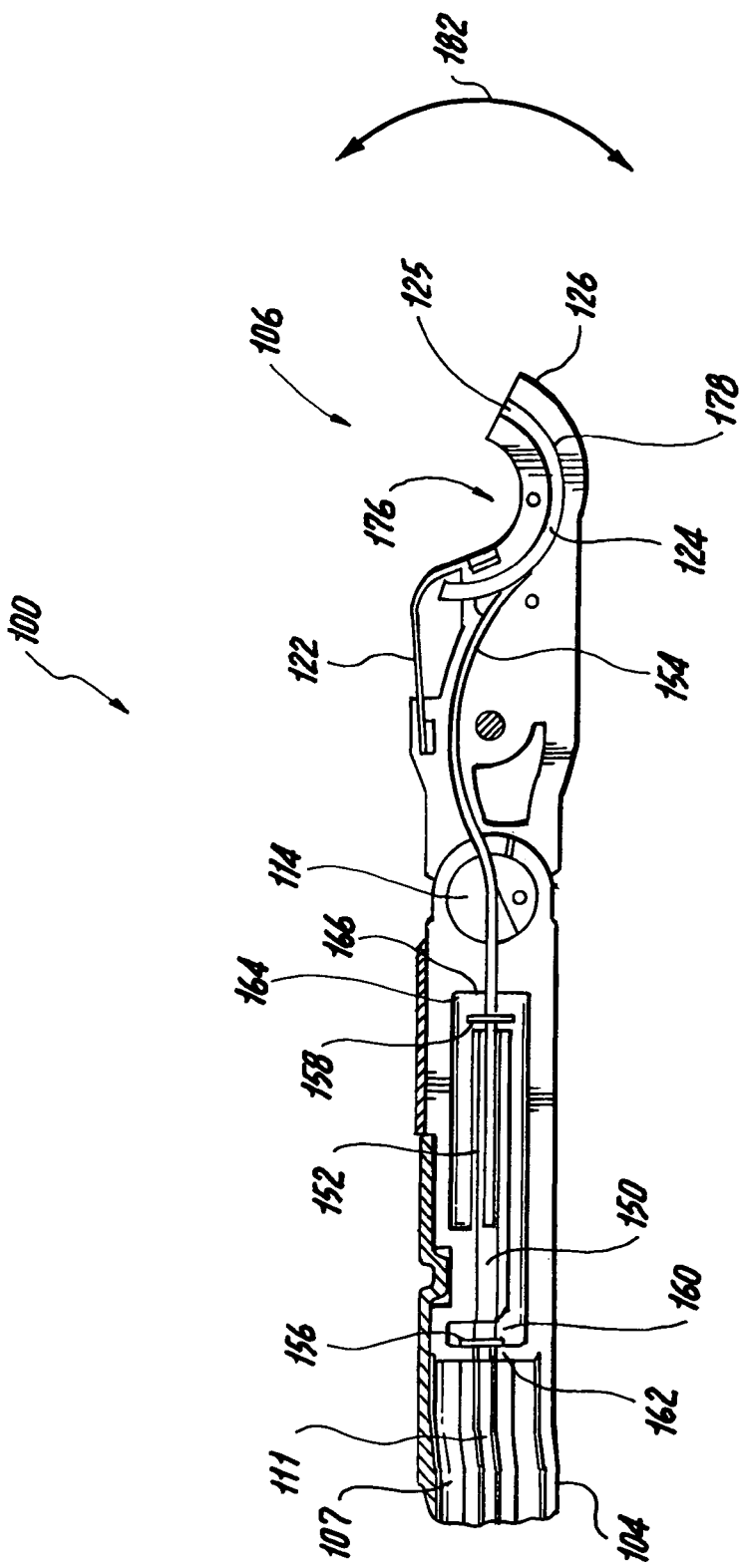

An embodiment of a delivery instrument 100 is shown in FIGS. 1A-1C. FIG. 1A depicts a delivery instrument 100 including a handle 102, an elongate body member 104, and a fixation head deployment mechanism 110. The delivery instrument 100 also includes a distal portion 106 and a proximal portion 108. The elongate body member 104 is mechanically coupled to the handle 102 at the proximal portion 108 and the delivery components are at least partially disposed within the distal portion 106 of the delivery instrument 100.

As shown in FIG. 1A, a fixation device 306 is engaged to the distal portion 106 of the delivery instrument 100 by placing the fixation device head 328 in an extendable carrier (shown in FIG. 1C). The carrier 124 comprises a side slot. When coupling the fixation device 306 to the carrier 124, the shaft 300 of the fixation device 306 is sized to pass through the side slot and the fixation device head 328 is positioned on top of an opening at a distal end of the carrier. The diameter of the fixation device head 328 is larger than the diameter of a lumen of the carrier. As such, the fixation device head 328 is positioned over the distal opening of the carrier while a portion of the shaft 300 of the fixation device resides within the lumen of the carrier. As such, when the fixation head deployment mechanism 110 is depressed, the carrier 124 drives the fixation device head 328 through a tissue until the fixation device head 328 is secured in a catch. Once secured in a catch, the carrier retracts to its original position and thus disengages from the fixation device head 328. Once the fixation device head 328 is secured in the catch, the delivery instrument 100 may be withdrawn a distance to pull the fixation device 306 a desired distance through the tissue. Finally, the fixation device head 328 is disengaged from the carrier once the fixation device has been successfully placed in a tissue. An embodiment of these components will be shown in detail in FIGS. 1B and 1C.

The handle 102 of the delivery instrument 100 could take a variety of forms, for example, the handle 102 could be one of the types used with Boston Scientific Corporation suturing systems, in particular the Capio® Push & Catch suturing system. Generally, the fixation device deployment mechanism 110 extends longitudinally through the elongate body member 104 to the distal portion 106 of the delivery instrument 100, where the fixation device head deployment mechanism 110 is coupled to a carrier 124 (FIG. 1C). The fixation device head deployment mechanism 110 moves the carrier 124 between a retracted position and a extended position. The fixation device deployment mechanism 110 is shown in greater detail in FIGS. 1B and 1C.

Referring to FIG. 1B, the proximal portion 108 of the delivery instrument 100 includes the handle 102, the elongate body member 104, and the fixation device deployment mechanism 110. The fixation device deployment mechanism 110 includes an actuator 112 (button 117, shaft 116), a bearing 118, a button end 119, and a hole 121. The bearing 118 rides along a cylindrical surface 105 that is formed by the inside diameter of the elongate body member 104. A wireform 103 is inserted into the hole 121, coupling it to the actuator button 117. A spring 115 encircles the wireform 103, abuts the button end 119, and is compressed between the button end 119 and a spring washer 113. The spring washer 113 is seated upon a center tube 107. The center tube 107 is housed by the cylindrical surface 105 and is constrained in the distal portion 106. A pusher wire 111 is attached to the wireform 103 by means of a weld, a coupling, adhesive or other means, and is slidably disposed within a guidance sleeve 109, the sleeve 109 being disposed within a cylindrical surface 123 formed by the inside diameter of the center tube 107. In an embodiment, the pusher wire 111 is constructed of nitinol, so chosen for its combination of properties that allow for bendability and high column strength when constrained. Nitinol is a nickel-titanium alloy. Those skilled in the art will recognize that a wire made of various materials are within the spirit and scope of the present invention.

Referring to FIG. 1C, the distal portion 106 of the delivery instrument 100 of FIG. 1A includes the elongate body member 104, the fixation device deployment mechanism 110, an articulation mechanism 114, a curved portion 126, and a catch 122. Referring again to the fixation device deployment mechanism 110, the pusher wire 111 is attached by welding or other means to a coupling 150, which is slidably disposed within a track 152. The coupling 150 is attached to a carrier wire 154, which by virtue of its attachment to the coupling 150 is also slidably disposed within the track 152. The carrier wire 154 is mechanically coupled to an extendable carrier 124 by means of a weld, a coupling, adhesives, or other means. The coupling 150 abuts a backstop washer 156 that is slidably disposed about the pusher wire 111 and is contained within a pocket 160 that includes a back wall 162, against which the backstop washer 156 rests. The track 152 terminates distally in a pocket 164 that includes a wall 166. A downstop washer 158 is slidably disposed about the carrier wire 154 and constrained within the pocket 164.

In some embodiments, the delivery instrument 100 may include the articulation mechanism 114. The articulation mechanism 114 is disposed in the elongate body member 104 proximate the distal portion 106 (FIG. 1C). The articulation mechanism 114 facilitates the rotation (in the directions indicated by arrow 182) and positioning of the distal end 106 of the delivery instrument 100. In addition, the elongate body 104 can be substantially linear or may include one or more bends. The articulation mechanism 114 and/or bend(s) can facilitate access to deep and/or difficult to reach areas within the patient.

FIG. 1C shows a distal opening 125 of the carrier 124. As discussed above, the carrier comprises a side slot which begins at the distal opening 125. In addition, the curved section 126 of the distal end comprises a slot 127 (shown in FIG. 3) which aligns with the side slot of the carrier 124. Aligning the slot of the carrier with the slot of the curved section 126 allows the shaft 300 of the fixation device to reside within a portion of the carrier while the fixation device head 328 rests on top of the distal opening 125 of the carrier (as shown in FIG. 1A and FIG. 2).

Figure 2:
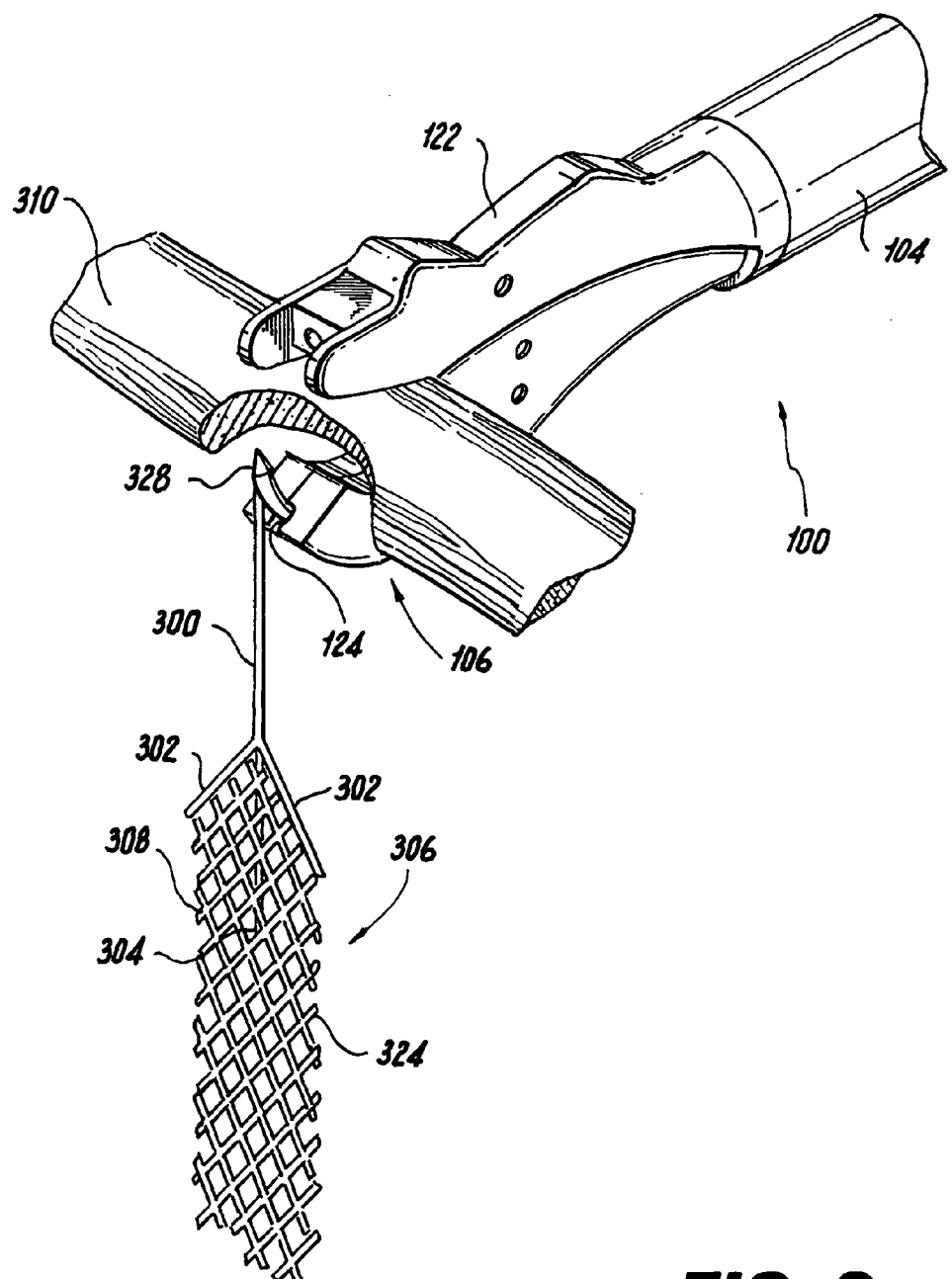
FIG. 2 shows an embodiment of a fixation device engaged to a delivery instrument.

FIG. 2 shows a presently disclosed embodiment of a delivery instrument 100 engaged to a fixation device 306. The fixation device 306 is engaged to the delivery instrument 100 by inserting the fixation device head 328 into an extendable carrier 124. As described above in relation to FIGS. 1A-1C, the extendable carrier 124 may be in a retracted position or an extended position. As shown in FIG. 2, the extendable carrier 124 is in a retracted position.

As shown in FIG. 2, an embodiment of the fixation device 306 comprises a shaft 300 which runs from the fixation device head 328 and ends with the beginning of a sling material 324. In an embodiment, the sling material 324 is a mesh. In an embodiment, the sling material 324 is a graft. In an embodiment, the sling material 324 may comprise a drug. Those skilled in the art will recognize that various other materials are within the spirit and scope of the present invention.

When the fixation device head 328 is coupled to the delivery instrument 100, the shoulder of the fixation device head 328 rests on the front edge of the extendable carrier 124, while the flexible shaft 300 of the fixation device 306 slides into the extendable carrier 124 through a slot and exits by a side port. The length of the flexible shaft 306 can vary depending on the need to exit the body for reloading for securing an additional fixation device 306.

In the embodiment shown in FIG. 2, a first and a second protrusion 302 extend from the flexible shaft 300 to encapsulate the sling material (i.e., a mesh or graft) and act as a leading edge. In an embodiment, the leading edge is stiffer than the sling material and angled to provide support to keep the sling material width extended yet collapsible to follow the flexible shaft 300 through a ligament and/or tissue 310. The ends of the leading edge 302 can also act as a barb for anchoring the fixation device 306 in place.

In an embodiment, the flexible shaft 300 extends through the sling material and act as a backbone or support segment 304. The backbone segment 304 provides strength to the sling material 324 to prevent the sling material 324 from unraveling as the fixation device 306 is pulled through a tissue and/or ligament 310.

In an embodiment, the sling material 324 comprises a plurality of tangs 308. The tangs 308 engage the tissue and/or ligament 310 in order to help secure the fixation device 306 to the tissue and/or ligament 310.

In an embodiment, the fixation device 306 comprises a medical grade, implantable polypropylene. In an embodiment, the fixation device 306 comprises a bio-absorbable material. Those skilled in the art will recognize that various materials are within the spirit and scope of the present invention.

FIG. 2 shows an embodiment wherein the delivery instrument 100 comprises the extendable carrier 124 in a retracted orientation. By engaging the fixation device deployment mechanism 110 (discussed above in relation to FIGS. 1A-1C), the extendable carrier 124 is extended full to allow the fixation device head 328 to pierce ligament or tissue and be received in the catch 122. As will be shown below, the pointed fixation device head 328 spreads the slot of the catch 122 as it passes into the catch 122. The slot then narrows as the extendable carrier 124 retracts, trapping the head by its wider shoulder within the catch 122 (see FIGS. 9A and 9B).

Figure 3:
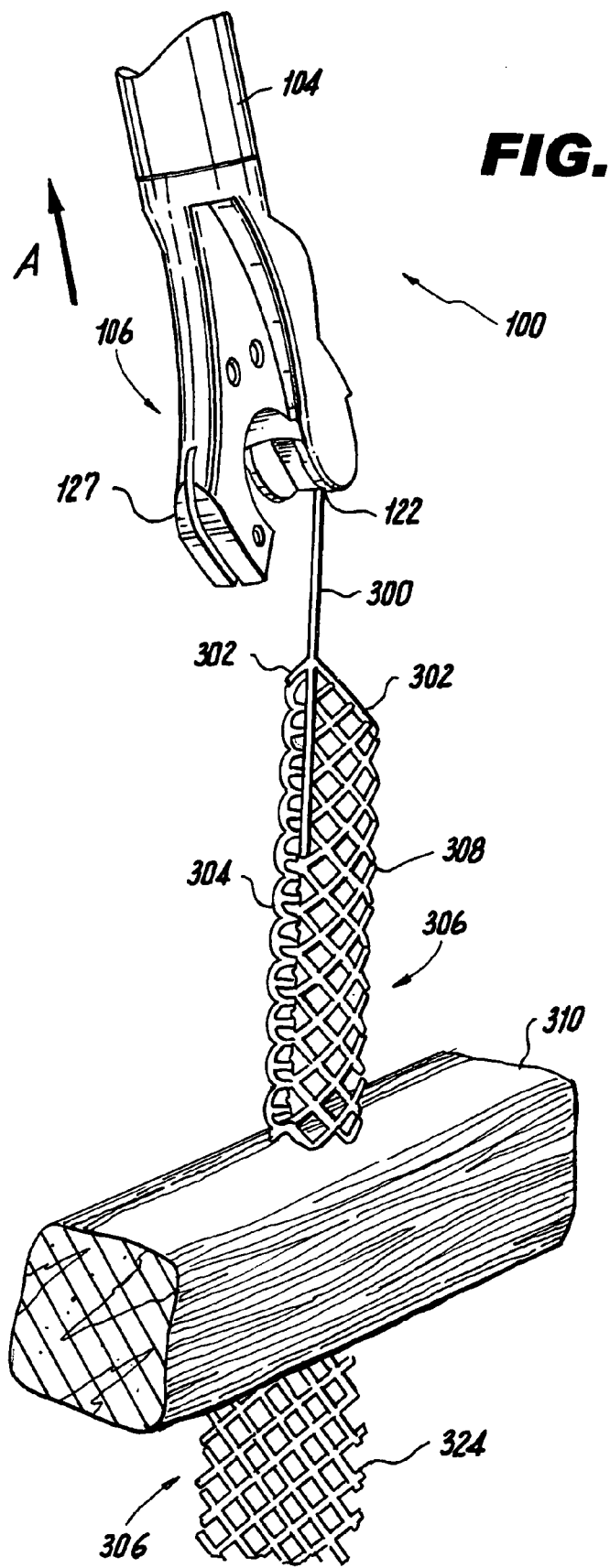
FIG. 3 shows an embodiment wherein the fixation device has passed through a tissue, a fixation device head has been engaged in a catch of a delivery instrument, and the fixation device is being pulled through a tissue and/or a ligament by withdrawing the delivery instrument.

FIG. 3 shows an embodiment of the presently disclosed delivery instrument 100 wherein the fixation device head 328 has passed through a tissue 310 and is now secured in the catch 122. Once the fixation device head 328 is retained in the catch of the delivery instrument 100, the delivery instrument 100 is pulled away from the treatment area in the general direction of arrow "A". As the delivery instrument 100 is withdrawn from the tissue and/or ligament 310, the fixation device 306 is drawn through the ligament and/or tissue 310. The fixation device 306 is drawn through the ligament/tissue until a desired length of fixation device is achieved for the proper suspension and/or tension.

In an embodiment, the fixation device 306 may be cut with a cutting instrument to remove any unwanted material. The fixation device 306 and the portion of the cut fixation device is retrieved external to the body through the exit port of the catch 122. In an embodiment, the delivery instrument 100 can be used for placement of additional fixation devices or needled sutures in the same patient.

Figure 4:
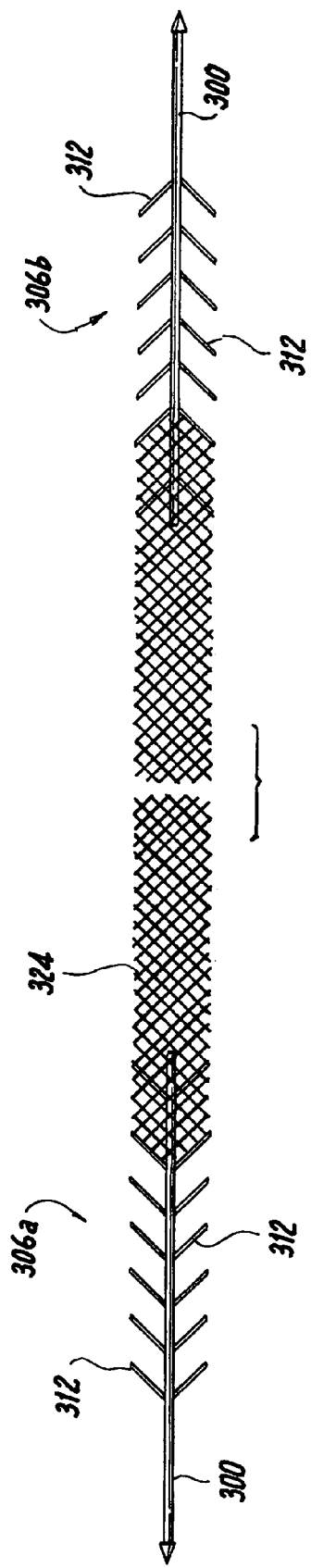
FIG. 4 shows an embodiment of a fixation device wherein the fixation device comprises a plurality of barbs.

FIG. 4 shows a presently disclosed embodiment wherein a first fixation device 306*a* is engaged to a first end of a sling 324 and a second fixation device 306*b* is engaged to a second end of a sling 324. In an embodiment, a fixation device 306 is insert molded onto the sling material 324.

In an embodiment, the sling is an incontinence sling. Those skilled in the art will recognize that any type of sling is within the spirit and scope of the present invention.

In an embodiment, the presently disclosed delivery instrument 100 is used to place the sling ends through Cooper's ligament in a manner similarly described above and repeated on the contra lateral side. In an embodiment, the sling can be threaded in and out of the transobturators using a delivery instrument 100 via a single incision vaginal approach using a fixation device having a longer flexible shaft as shown in FIG. 4, for tensioning afterwards, through a mid-line incision.

In an embodiment as shown in FIG. 4, a plurality of barbs 312 are positioned along the shaft 300 of each fixation device 306a, 306b. The tissue and/or ligament may be anchored to by the barbs 312 positioned along the flexible shaft 300.

Figure 5:
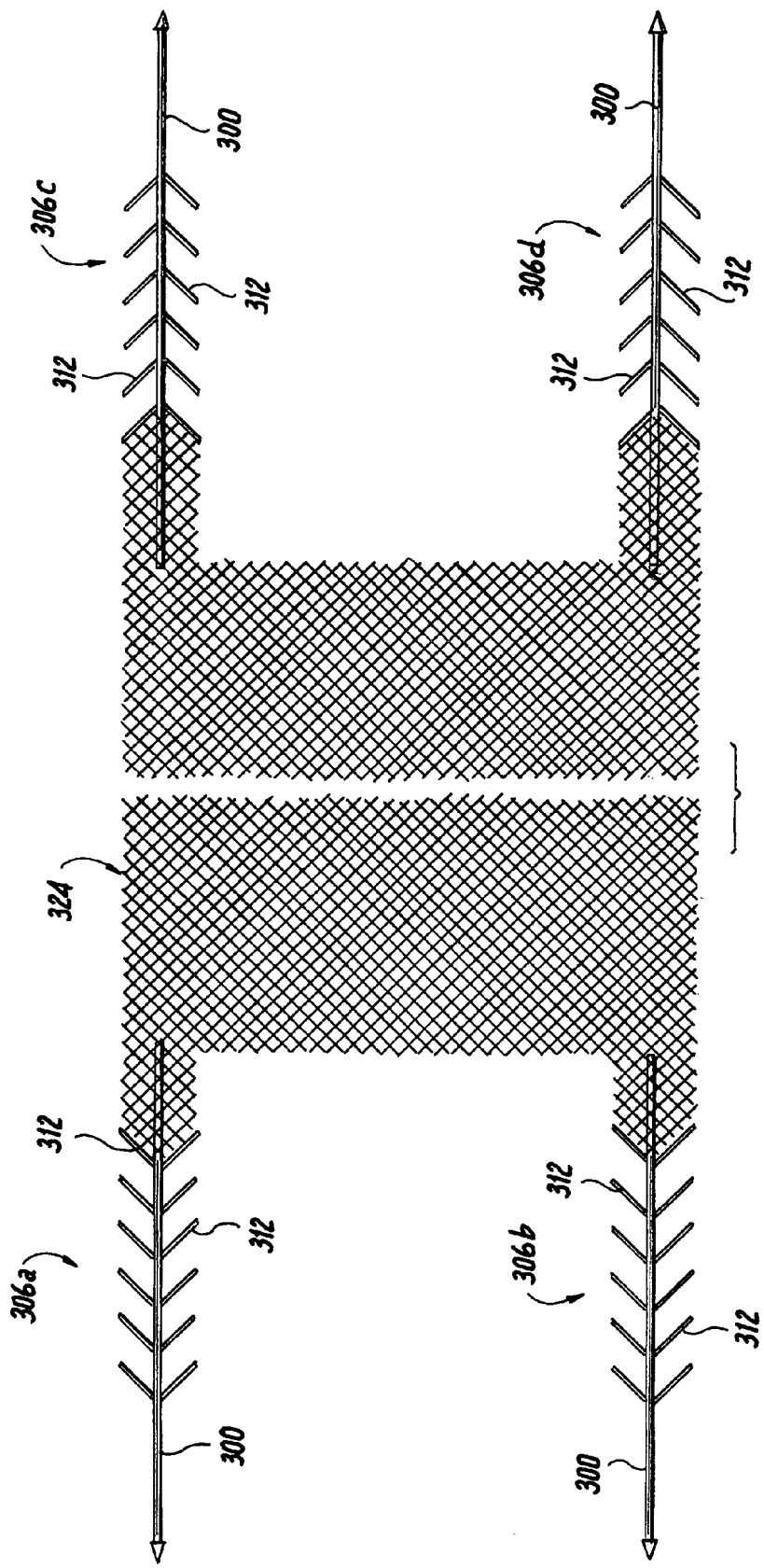
FIG. 5 shows an embodiment wherein a plurality of fixation devices are engaged to a graft.

FIG. 5 shows a presently disclosed embodiment wherein a plurality of fixation devices 306a, 306b, 306c and 306d are engaged to a plurality of locations of a graft 324. In an embodiment, the fixation devices are 306a, 306b, 306c and 306d are insert molded onto a graft. Those skilled in the art will recognize that various processes may be used to engage a fixation device 306 to the graft and remain within the spirit and scope of the present invention.

The graft can be used for anterior or posterior repairs wherein the fixation devices 306a, 306b, 306c and 306d can be anchored to the sacrospinous ligament, Cardinal ligament, uterosacral ligament or other tissues and ligament to suspend the graft to support and repair prolapses and enterceles.

Each fixation device 306a, 306b, 306c and 306d is placed individually at the discretion of the user by drawing the fixation device 306a, 306b, 306c and 306d through ligament of tissue until the desired length of "leg" is achieved. As such, a head of the first fixation device 306a is engaged to the delivery instrument 100, driven through a tissue, secured in a catch, positioned in the tissue by withdrawing the delivery instrument 100, and disengaged from the catch. Next, the head of the second fixation device 306b is engaged to the delivery instrument 100 and the steps are repeated. The above-identified procedure is followed for all additional fixation devices 306c, 306d, etc.

In an embodiment, the graft is centered over the enterocele. In an embodiment, the graft is suspended non-taut.

Figure 6:
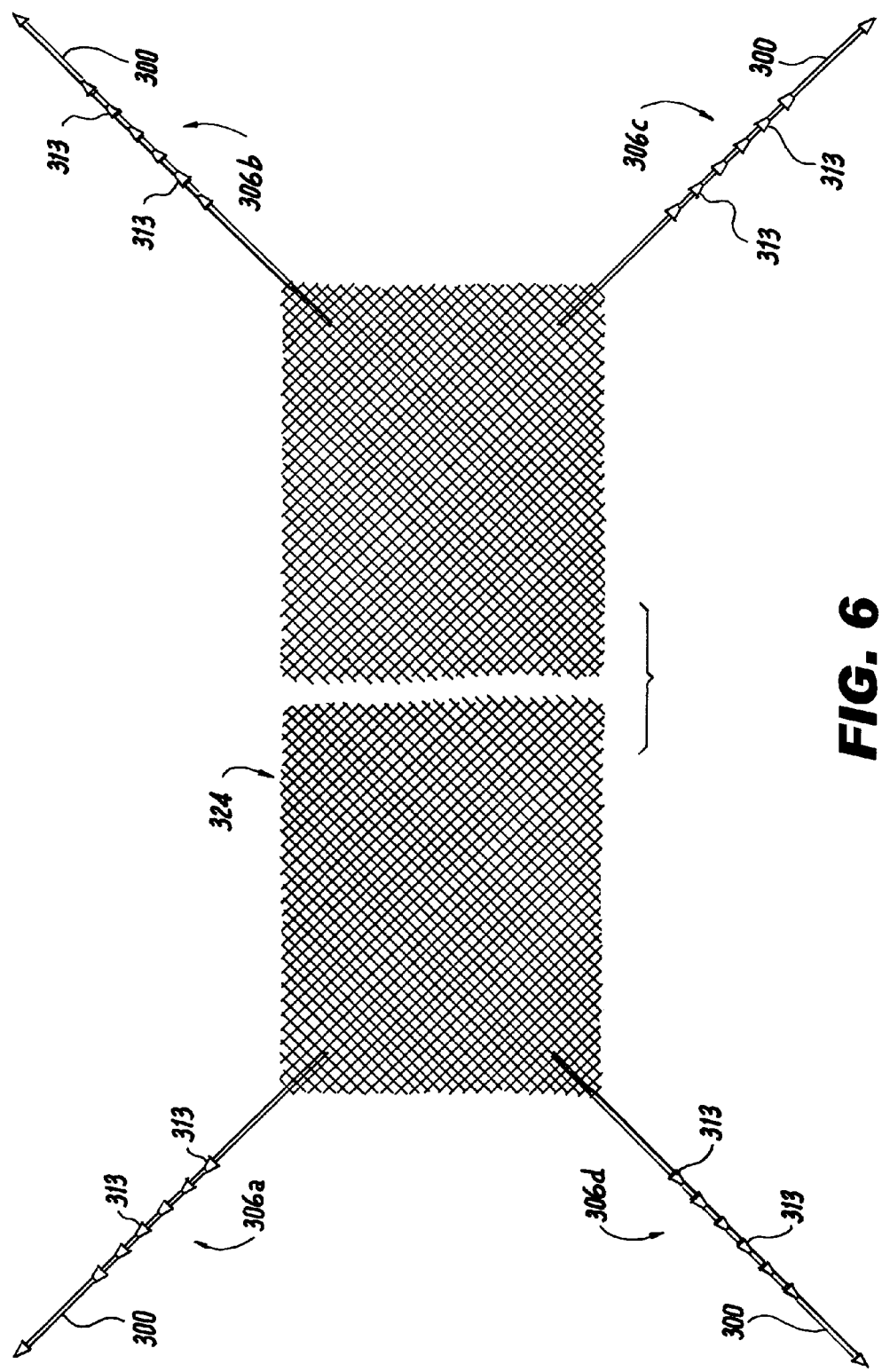
FIG. 6 shows another embodiment wherein a plurality of fixation devices are engaged to a graft.

FIG. 6 shows a presently disclosed embodiment wherein a plurality of fixation devices 306a, 306b, 306c, and 306d are engaged to graft 324. In comparison to the fixation devices 306a, 306b, 306c and 306d shown in FIG. 5, the fixation devices 306a, 306b, 306c and 306d do not comprise a plurality of barbs 312; rather, the various shafts 300 comprise a plurality of protrusions 313 which allow the user to engage a desired protrusion 313 to the catch 122 to achieve a desired tension. As such, the position and the desired tension of the graft 324 is achieved by displacement of the draw of each fixation device 306a, 306b, 306c and 306d through a tissue and/or ligament. Additional draw can create tension in the graft 324.

The size and shape of the various components of a fixation device 306 and/or sling material 324 can vary for different applications. The shaft 300 length can vary from about 1 cm to about 120 cm. In an embodiment, the shaft 300 length is greater than about 120 cm. The longer shaft 300 length enables a second fixation device 306b to be withdrawn from the body after the first placement of the first fixation device 306a in order to be reloaded onto the carrier 124. The second fixation device 306b can also be placed into a different location to create a "suture bridge" for approximation or suspension.

Figure 7:
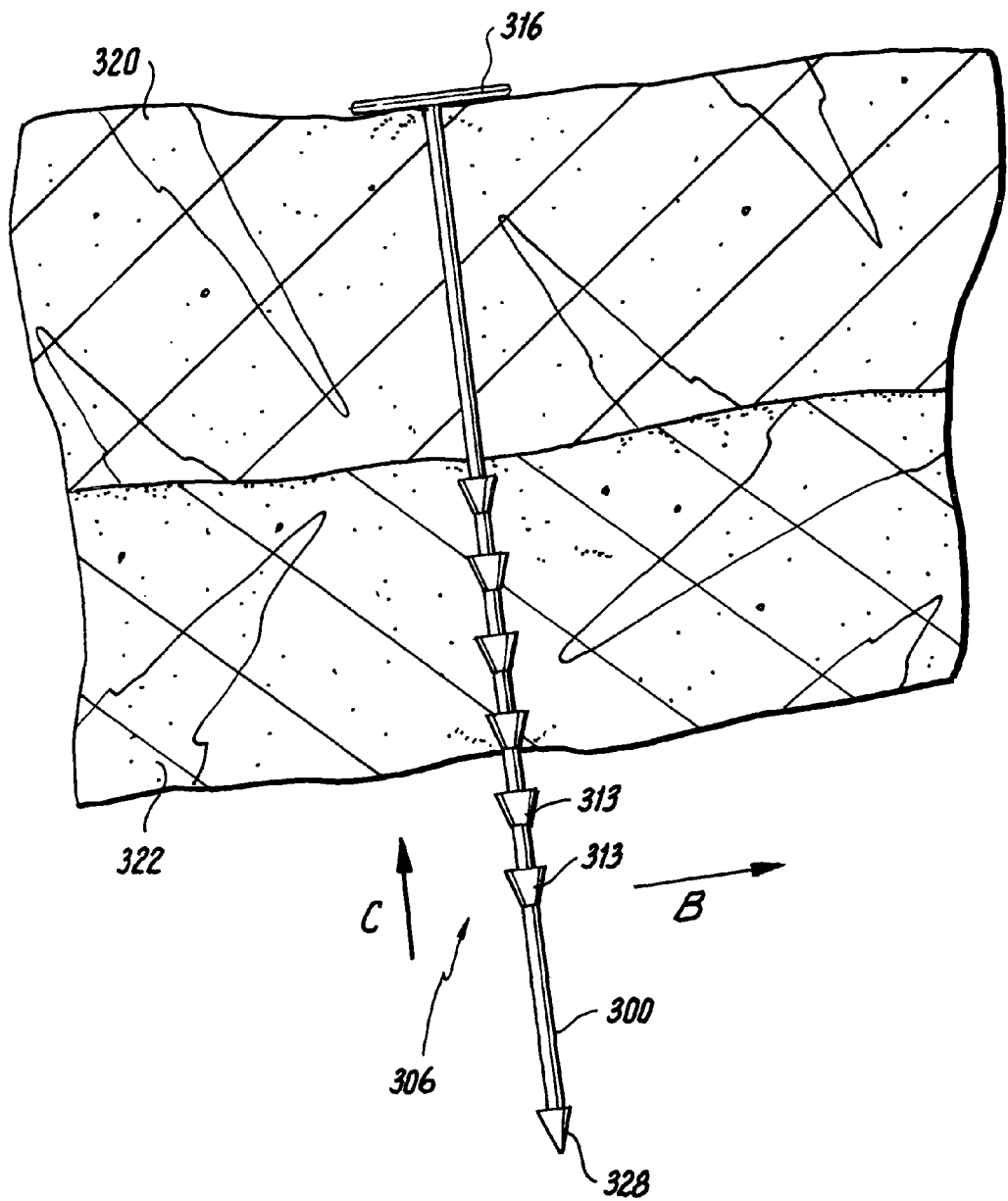
FIG. 7 shows an embodiment of a fixation device comprising a T-shaped protrusion wherein the fixation device is not engaged to a sling material.

FIG. 7 shows a presently disclosed embodiment wherein the fixation device 306 is a separate unit. The fixation device head 328 is sized and shape fitted to the carrier 124 of the delivery instrument 100. The circular protrusions 313 allow tissue to pass in one direction and anchors in the opposing direction. A backstop 316 is provided to abut against tissue to prevent the fixation device 306 from passing through the tissue. In an embodiment, the backstop 316 is a circular shape. In an embodiment, the backstop 316 is a T-shaped protrusion. Those skilled in the art will recognize that any a backstop of any shape which prevents the fixation device from passing through the tissue is within the spirit and scope of the present invention.

FIG. 7 shows a presently disclosed embodiment wherein a fixation device 306 pierces a first tissue 320 and a second tissue 320 with a single "throw" of the delivery instrument 100. In an embodiment, the first tissue 320 is pierced by a first throw of the delivery instrument 100 and the second tissue 322 is pierced by a second throw of the delivery instrument 100. The head may be pulled in a direction represented by arrow "B" to force the second tissue 322 to approximate to the first tissue 320. In an embodiment, a rod or a stabilizer can be used in the direction of arrow "C" to approximate the first tissue 320 to the second tissue 322.

In an embodiment, the fixation device 306 is secured in place with a button (not show) slid down over the shaft 300 to engage a desired barb 313.

Figure 8:
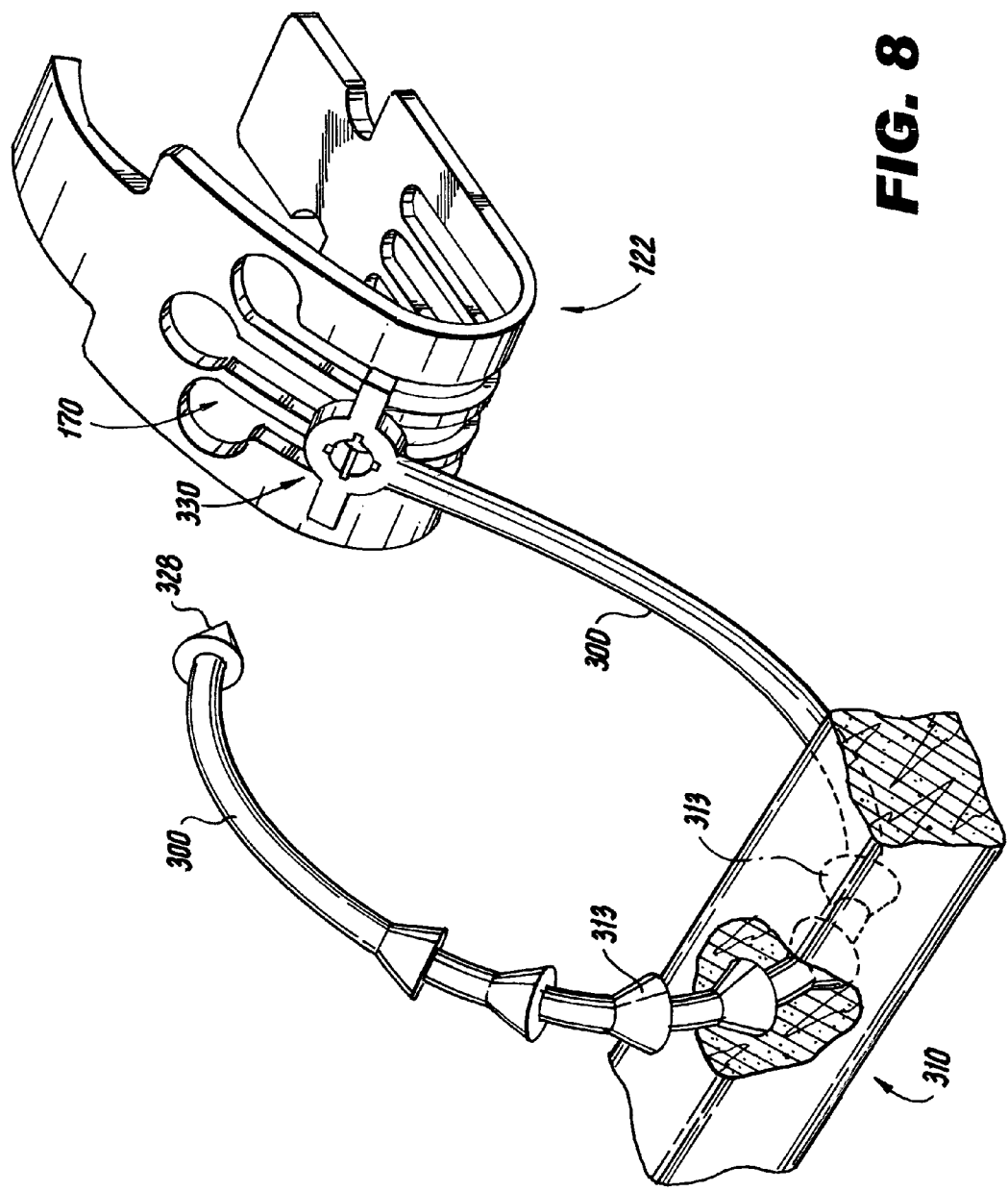
FIG. 8 shows an embodiment of a fixation device and a lock button wherein the lock button engages a protrusion on the fixation device.

FIG. 8 shows a lock button 330 incorporated into an embodiment of the presently disclosed fixation device 306. In an embodiment, the lock button 330 is positioned to receive the carrier 124 and fixation device head 328. The lock button 330 has a lock diameter larger than the fixation device head 328 and carrier 124 such that the carrier 124 and fixation device head 328 pass though the lock button 330 freely but is sized to be received by the catch 124. To lock, the fixation device head 328 is pulled to draw the shaft 300 through the lock hole 330 to engage the locking barbs 313. Further drawing indexes to the next barb 313 tightening the resulting loop. Excess loop is trimmed.

Figure 9A:
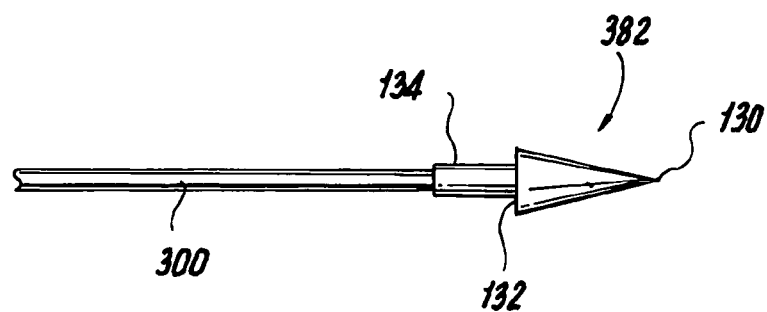
FIG. 9A is a schematic plan view of a fixation device head coupled to a shaft for use in a delivery instrument in accordance with the invention.

Referring to FIG. 9A, in one embodiment, the fixation device head 328 includes a tip 130 and a shaft 134 coupled to the tip 130, thereby forming a shoulder 132. The shaft 134 is coupled to a shaft 300. The fixation device head 328 is inserted into the lumen 138 and held by a slight friction fit.

Figure 9B:
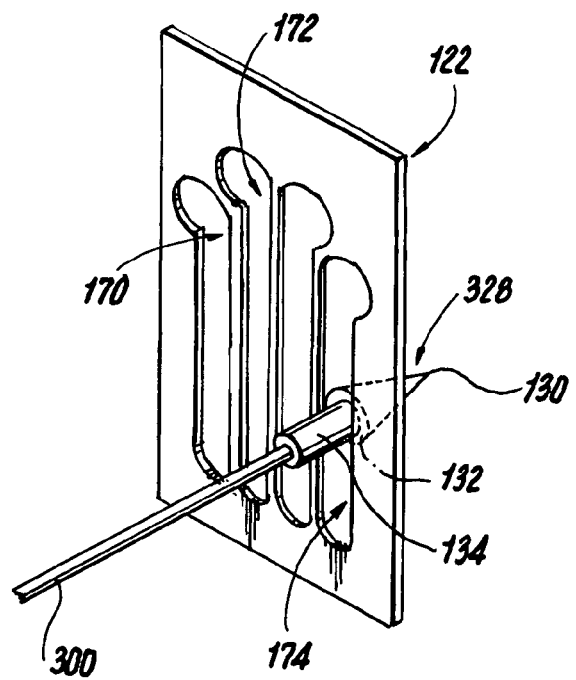
FIG. 9B is a schematic perspective view of a catch for use with the delivery instrument of FIG. 1A.

Referring again to FIGS. 1B and 1C, in operation, a user (such as a physician or other medical personnel) actuates the fixation device deployment mechanism 110 by pushing on the button 117, which via the attachment to the wireform 103 which is attached to the pusher wire 111, moves the coupling 150 along the track 152 concomitantly moving the carrier wire 154, which slidably moves the extendable carrier 124 through the exit port 120. The user continues to push the button 117 until the fixation device head 328 enters the catch 122. The catch 122, as shown in FIG. 9B, includes openings 170 defined by successive ribs 172. The catch 122 receives the fixation device head 328 (coupled to the shaft 300 of the fixation device 306) through opening 170, the ribs 172 deflect slightly to allow the fixation device head 328 to pass through. After the formed shoulder 132 has passed the ribs 172, the ribs 172 spring back to their original position defining the openings 170, and the fixation device head 328 remains captured in the catch 122. The user releases the button 117 and the spring 115 urges the button 117 proximally, moving the pusher wire 111, the coupling 150, the carrier wire 154, and the carrier 124 proximally along with the button 117 to the retracted position. As the extendable carrier 124 moves back to the retracted position, the fixation device head 328 slides out of the carrier.

The openings 170 are chosen to be smaller in dimension than the formed shoulder 132. This causes the catch 122 to retain the fixation device head 328 because the flat rear surface of the shoulder 132 prevents the fixation device head 328 from passing back through the opening 170. When it is necessary to remove the fixation device head 328 from the catch 122, the fixation device head 328 may be moved toward an enlarged portion 174 of opening 172. The enlarged portion 174 is sized to allow the formed shoulder 132 to pass through without resistance. The catch 122 is preferably constructed of thin stainless steel of high temper, such as ANSI 301 full hard. The catch 122 may be fabricated by means of stamping, laser machining, or chemical etching. Those skilled in the art will recognize that the catch may be comprise a wide range of materials and remain within the spirit and scope of the present invention; further, those skilled in the art will recognize that the catch may be fabricated by a wide range of methods and remain within the spirit and scope of the present invention.

The delivery instrument's component materials should be biocompatible. For example, the handle 102, the elongate body member 104, and portions of the fixation device head deployment mechanism 110 may be fabricated from extruded, molded, or machined plastic material(s), such as polypropylene, polycarbonate, or glass-filled polycarbonate. Other components, for example the fixation device head 328, may be made of stainless steel. Other suitable materials will be apparent to those skilled in the art. Additionally, the mechanical components and operation are similar in nature to those disclosed in U.S. Pat. Nos. 5,364,408 and 6,048,351, each of which is incorporated by reference herein in its entirety.

Certain embodiments according to the invention have been disclosed. These embodiments are illustrative of, and not limiting on, the invention. Other embodiments, as well as various modifications and combinations of the disclosed embodiments, are possible and are within the scope of this disclosure.

What is claimed is:

1. An instrument for delivering an implant to tissue of a patient, comprising:
   an elongate body member;
   a deployment mechanism disposed at a distal portion of the elongate body member, the deployment mechanism including a carrier capable of extending from a retracted position to an extended position, the carrier comprising a side slot for receiving a portion of a fixation device of the implant, the fixation device including a head engaged to a flexible shaft, and a first and second protrusion extending from the flexible shaft, the first and second protrusions each being angled relative to a longitudinal axis of the flexible shaft and collectively encapsulating a distal end of a sling material of the implant, the distal portion of the elongate body member having a slot that is disposed adjacent to and in alignment with the side slot of the carrier when the carrier is in its refracted position, the first and second protrusions defing a T-shaped protrusion having a lock button disposed therein, the flexible shaft including a plurality of circular protrusions disposed thereon for engaging the lock button; and
   a catch disposed on the elongate body member, the catch defining at least one opening for receiving, through the lock button, the carrier holding the fixation device, retaining the head of the fixation device within the catch, and allowing the carrier to retract, such that the fixation device is released from the side slot of the carrier when the carrier is retracted from the catch.

2. The instrument of claim 1, wherein the sling material comprises a mesh material.

3. The instrument of claim 2, wherein the mesh material comprises a plurality of tangs.

4. The instrument of claim 1, wherein the sling material comprises a graft.

5. The instrument of claim 1, wherein the flexible shaft comprises a plurality of barbs.

6. The instrument of claim 1, wherein the of the fixation device includes a pointed tip.

7. The instrument of claim 1, wherein the head of the fixation device is sized to be received by the carrier of the deployment mechanism.

8. The instrument of claim 1, wherein the flexible shaft extends into at least a portion of the sling material forming a support segment to provide strength to the sling material.

9. The instrument of claim 1, wherein the slot of the distal portion of the elongate body member is sized to allow a portion of the flexible shaft of the fixation device to extend through the slot of the distal portion from the carrier to an area external to the distal portion of the elongate body member.

10. The instrument of claim 1, wherein the first protrusion and the second protrusion define a proximal end of the fixation device, the proximal end of the fixation device being movable between a first width and a second width less than the first width, the proximal end of the fixation device being biased to the first width.

11. The instrument of claim 1, wherein the slot of the distal portion of the elongate body is disposed distally of the side slot of the carrier when the carrier is in its retracted position.

* * * * *